United States Patent [19]

Hama et al.

[11] Patent Number: 5,708,181
[45] Date of Patent: Jan. 13, 1998

[54] SPIROPYRAN COMPOUND

[75] Inventors: Hiroshi Hama, Naruto; Shinji Nakano, Tokushima, both of Japan

[73] Assignee: Otsuka Kagaku Kabushiki Kaisha, Osaka, Japan

[21] Appl. No.: 532,802
[22] PCT Filed: Mar. 10, 1995
[86] PCT No.: PCT/JP95/00396
§ 371 Date: Nov. 8, 1995
§ 102(e) Date: Nov. 8, 1995
[87] PCT Pub. No.: WO95/24409
PCT Pub. Date: Sep. 14, 1995

[30] Foreign Application Priority Data

Mar. 11, 1994 [JP] Japan ................ 6-040263

[51] Int. Cl.⁶ ............................. C07D 517/10
[52] U.S. Cl. ................................. 548/121
[58] Field of Search ........................ 548/121

[56] References Cited

FOREIGN PATENT DOCUMENTS 2078685  3/1990  Japan .

*Primary Examiner*—Robert Gerstl
*Attorney, Agent, or Firm*—Armstrong, Westerman, Hattori, McLeland & Naughton

[57] ABSTRACT

An object of the present invention is to provide a novel compound which is suitably usable as a photochromic material.

The compound of the present invention is a salt of a spiropyran compound and an acidic compound, the spiropyran compound being represented by the formula

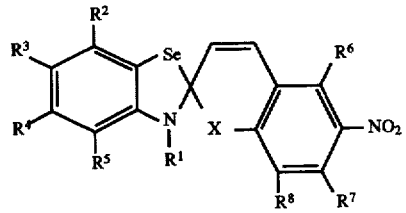

wherein $R^1$ means a $C_1$ to $C_{20}$ alkyl group, an aralkyl group, a hydroxyethyl group, an acryloxyethyl group or a methacryloxyethyl group, $R^2$ to $R^7$ each mean a hydrogen atom, a $C_1$ to $C_6$ alkyl group or the like, $R^8$ means a hydrogen atom, a vinyl group, a group $-CH_2OR^9$ or a group $-CH_2OCOC(R^{10})=CH_2$ (wherein $R^9$ means a hydrogen atom or a $C_1$ to $C_4$ alkyl group and $R^{10}$ means a hydrogen atom or a methyl group), and X means an oxygen atom or a sulfur atom.

2 Claims, 6 Drawing Sheets

Wavelength(nm)

SPIROPYRAN COMPOUND

This application is a 371 of PCT/JP95/00396 filed Mar. 10, 1995.

TECHNICAL FIELD

The present invention relates to a spiropyran compound showing negative photochromism.

BACKGROUND ART

Photochromism is a phenomenon wherein a material reversibly changes in absorption spectrum by light irradiation. Spiropyran derivatives are typical and best known organic compounds showing such a phenomenon. For specific examples and physical properties of said derivatives, G. H. Brown: Photochromism (John Wiley & Sons, Inc. 1971) can be consulted, for example. Most of said derivatives show normal photochromism, i.e., a characteristic of being colorless at the normal state but colored by ultraviolet irradiation.

On the other hand, benzoselenazoline-type spiropyran compounds are known as typical compounds showing negative photochromism. Thus, said compounds have a color at the normal state, lose their color by irradiation with visible light and revert to the original colored state by subsequent ultraviolet irradiation or heating. Said compounds are disclosed, for example, in Japanese Unexamined Patent Publications No. 78685/1990 and No. 289587/1990, Published Searched Application No. 813072/1991 and the like. However, all of the known compounds have the maximum absorption wavelength at 500 to 600 nm, and no compounds have been found which are highly sensitive to visible light or a laser beam in the wavelength region of 400 to 500 nm.

Recently, an attempt has been made to use a compound showing photochromism (hereinafter referred to as "photochromic compound") as optical materials such as optical information recording media, optical filters and the like. However, as mentioned above, the conventionally known photochromic compounds have the maximum absorption wavelength at 500 nm or more. In view of increasing demands for recording in higher density and developing second harmonic generation materials (hereinafter referred to as "SHG materials") which shorten or convert the wavelength of a semiconductor laser beam, photochromic compounds which are sensitive (or responsive) to light of shorter wavelengths have been demanded.

DISCLOSURE OF THE INVENTION

An object of the present invention is to provide a compound which has the maximum absorption wavelength at 400 to 500 nm and is highly sensitive to light in said wavelength region.

The compound of the present invention is a novel compound which has not been disclosed in any literature, the compound being a salt of a benzoselenazoline-type spiropyran compound of the formula (1) (hereinafter briefly referred to as "spiropyran compound (1)") and an acidic compound.

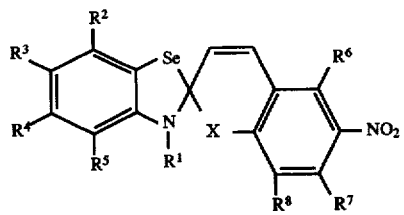

wherein $R^1$ means a $C_1$ to $C_{20}$ alkyl group, an aralkyl group, a hydroxyethyl group, acryloxyethyl group or a methacryloxyethyl group, $R^2$ and $R^4$ are the same or different and each mean a hydrogen atom, a $C_1$ to $C_6$ alkyl group, an aryl group, an aralkyl group, a $C_1$ to $C_5$ alkoxy group, a halogen atom, a cyano group, a trichloromethyl group, a trifluoromethyl group or a nitro group, $R^3$ and $R^5$ are the same or different and each mean a hydrogen atom, a $C_1$ to $C_6$ alkyl group, an aryl group, an aralkyl group, a $C_1$ to $C_5$ alkoxy group, a halogen atom, a cyano group, a trichloromethyl group, a trifluoromethyl group, a nitro group, an amino group, a dimethylamino group or a diethylamino group, $R^6$ and $R^7$ may be the same or different and each mean a hydrogen atom, a $C_1$ to $C_6$ alkyl group, an aryl group, an aralkyl group, a halogen atom, a cyano group or a nitro group, $R^8$ means a hydrogen atom, a vinyl group, a group —$CH_2OR^9$ or a group —$CH_2OCOC(R^{10})=CH_2$ (wherein $R^9$ means a hydrogen atom or a $C_1$ to $C_4$ alkyl group and $R^{10}$ means a hydrogen atom or a methyl group), and X means an oxygen atom or a sulfur atom.

In formula (1), the $C_1$ to $C_{20}$ alkyl group represented by $R^1$ is a straight- or branched-chain $C_1$ to $C_{20}$ alkyl group, and specific examples include methyl, ethyl, n-propyl, iso-propyl, n-butyl, sec-butyl, tert-butyl, n-pentyl, n-hexyl, n-octyl, n-decyl, n-octadecyl and the like.

The aralkyl group represented by $R^1$ and $R^7$ includes, for example, benzyl, 1-phenethyl, 2-phenethyl, 3-phenylpropyl, 4-phenylbutyl and like phenylalkyl groups whose alkyl moiety is a straight- or branched-chain alkyl having about 1 to about 4 carbon atoms. The phenyl ring of the phenylalkyl group may have one or more substituents such as a straight- or branched-chain alkyl group having about 1 to about 4 carbon atoms, a straight- or branched-chain alkoxy group having 1 to about 4 carbon atoms, a halogen atom such as chlorine, bromine, iodine, etc., a nitro group and the like.

The $C_1$ to $C_6$ alkyl group represented by $R^2$ and $R^7$ includes, for example, a straight- or branched-chain alkyl group such as methyl, ethyl, n-propyl, iso-propyl, n-butyl, sec-butyl, tert-butyl, n-pentyl, n-hexyl and the like.

The aryl group represented by $R^2$ and $R^7$ includes, for example, phenyl, naphthyl and the like, among which phenyl is preferred. The aromatic ring of these groups may have one or more substituents such as a straight- or branched-chain alkyl group having about 1 to about 4 carbon groups, a straight- or branched-chain alkoxy group having about 1 to about 4 carbon atoms, a halogen atom such as chlorine, bromine, iodine, etc., a nitro group and the like.

The halogen atom represented by $R^2$ and $R^7$ includes, for example, chlorine, bromine, iodine and the like.

The $C_1$ to $C_5$ alkoxy group represented by $R^2$ and $R^5$ includes, for example, a straight- or branched-chain alkoxy group such as methoxy, ethoxy, n-propoxy, iso-propoxy, n-butoxy, sec-butoxy, tert-butoxy, n-pentyloxy and the like.

The $C_1$ to $C_4$ alkyl group represented by $R^9$ includes, for example, a straight- or branched-chain alkyl group such as methyl, ethyl, n-propyl, iso-propyl, n-butyl, sec-butyl, tert-butyl and the like.

The salt of spiropyran compound (1) and an acidic compound (hereinafter briefly referred to as "spiropyran compound salt") according to the present invention can serve as the objective photochromic compound, since it has the maximum absorption wavelength at 400 to 500 nm and shows high sensitivity to light in said wavelength region. The spiropyran compound salt of the invention normally has a color, rapidly loses its color by irradiation with visible light and reverts to the original colored state by ultraviolet irradiation or heating, showing negative photochromism. The cycle of negative photochromism of the spiropyran compound salt of the invention is stably repeated and reproduced in various organic solvents and resins.

In view of the above characteristics, the spiropyran compound salt of the invention can be used as a starting material for various optical materials such as high-density optical recording materials, record readout elements, optical filters, optical switches, pH sensors, gas sensors, image-forming materials, sensitized materials, nonlinear optical elements and the like, and its application to the fields such as conversion of optical energy to mechanical energy is expected. Further, it can be used as a decorating material, as well as an optical material.

Moreover, a combination of a semiconductor laser with a SHG material, a mercury lamp (405, 436 nm), an Ar laser (458, 477 nm), a Kr laser (407, 468 nm), a Cd laser (442 nm) or the like which emits visible light can be employed as the light source for photochromic reaction of the spiropyran compound salt of the invention, whereas such light sources can not be employed for photochromic reaction of conventional compounds since the conventional compounds are not sensitive to the visible light.

Among the spiropyran compound salts of the invention, preferred is a salt of an acidic compound and spiropyran compound (1) of formula (1) wherein $R^1$ means a methyl group, an ethyl group, a n-propyl group, a n-octadecyl group, a hydroxyethyl group or a methacryloxyethyl group, $R^2$ means a hydrogen atom, $R^3$ means a hydrogen atom, a methyl group, a methoxy group, a nitro group, an amino group, a dimethylamino group or a diethylamino group, $R^4$ means a hydrogen group, a methyl group or a methoxy group, $R^5$ means a hydrogen group, a nitro group, an amino group, a dimethylamino group or a diethylamino group, $R^6$ and $R^7$ each mean a hydrogen atom, $R^8$ means a hydrogen atom, a vinyl group, a hydroxymethyl group or a methacryloxymethyl group, X means an oxygen atom or a sulfur atom.

The spiropyran compound salt of the invention can be produced by a conventional method, for example, by reacting spiropyran compound (1) with an acidic compound. In particular, the spiropyran compound salt of the invention can be easily prepared using spiropyran compound (1) having an amino group as a substituent on the aromatic ring as a starting material.

A variety of conventionally known acidic compounds can be used for the reaction with spiropyran compound (1), insofar as they can undergo neutralization reaction with spiropyran compound (1) acting as an organic base. Examples of the acidic compounds include protonic acids, Lewis acids and the like, among which protonic acids are preferred. Variety of known protonic acids can be used, for example, hydrochloric acid, sulfuric acid, perchloric acid, benzenesulfonic acid, toluenesulfonic acid, chlorobenzenesulfonic acid, sulfonic acid type ion-exchange resins and the like. Among them, preferably used are hydrochloric acid, sulfuric acid, toluenesulfonic acid and the like.

The acidic compound may be used in a large excess of spiropyran compound (1). However, since the nitrogen atom on the selenazole ring of spiropyran compound (1) and the substituting amino group(s) (the number of the amino group(s) is represented by n, which is an integer of 0 to 2) of spiropyran compound (1) participate in the neutralization reaction, the acidic compound is used preferably in an amount of about 0.01 to about (n+5) equivalents, more preferably about 0.1 to about (n+1) equivalents per mole of spiropyran compound (1).

The reaction of spiropyran compound (1) with the acidic compound can be carried out without a solvent, but is carried out preferably in the presence of a solvent. Usable solvents are not limited specifically and include, for example, lower alcohols such as methanol, ethanol, propanol and the like, ethers such as tetrahydrofuran, dioxane, dimethoxyethane and the like, halogenated hydrocarbons such as dichloromethane, chloroform and the like, dimethylformamide, dimethylsulfoxide and the like, and mixtures of these solvents.

The amount of spiropyran compound (1) to be dissolved in the solvent is not limited specifically, but usually about 0.1 to about 30 g, preferably about 0.5 to about 10 g, with respect to 100 ml of the solvent.

The salt-forming reaction can be carried out at a temperature conventionally employed for a salt-forming reaction, i.e., about 0° C. to around room temperature. Generally, however, said reaction is preferably carried out at room temperature.

The spiropyran compound salt of the present invention is formed immediately on contact of spiropyran compound (1) with the acidic compound. Therefore, the product formed in the solvent can be used as a solution without isolation, and when isolation of the salt is required, the salt of the present invention can be collected simply by distilling off the solvent.

The spiropyran compound salt of the present invention can be thus obtained.

Spiropyran compound (1) used as the primary starting material for the spiropyran compound salt of the invention, as such, is a photochromic compound which has a maximum absorption wavelength at 500 to 600 nm.

Spiropyran compound (1) can be prepared by a conventional method disclosed, for example, in Japanese Unexamined Patent Publications No. 78685/1990 and No. 289587/1990, Published Searched Application No. 813072/1991 and the like.

The following reaction schema-1 shows one of known methods wherein spiropyran compound (1) is easily prepared by subjecting a benzoselenazolenium salt derivative of formula (2) and a 5-nitrosalicylaldehyde derivative of formula (3) to condensation reaction.

Reaction Schema-1

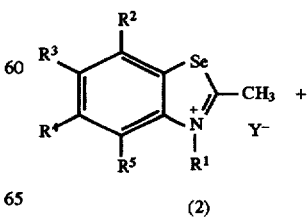

(2)

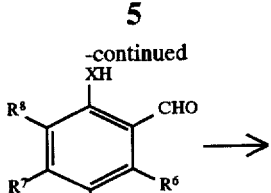

(3)

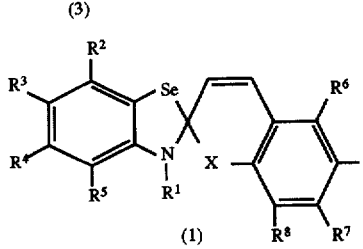

(1)

wherein $R^1$, $R^2$, $R^3$, $R^4$, $R^5$, $R^6$, $R^7$, $R^8$ and X are as defined above, and Y is a halogen atom or a group $R^{11}SO_3$— (wherein $R^{11}$ is a phenyl group which may be substituted by a halogen atom or a $C_1$ to $C_4$ alkyl group).

In formula (2), the halogen atom represented by Y includes, for example, chlorine, bromine, iodine and the like, among which iodine is preferred. When Y means a group $R^{11}SO_3$—, the examples of the halogen atom in the phenyl group represented by $R^{11}$ are the same as the above-exemplified halogen atoms. Preferred specific examples of the group $R^{11}SO_3$— include p-toluenesulfonic acid, p-chlorobenzenesulfonic acid and the like.

The benzoselenazolenium salt derivative of formula (2) (hereinafter referred to as "compound (2)") and the 5-nitrosalicylaldehyde derivative (hereinafter referred to as "compound (3)") are subjected to condensation reaction in the presence of an amine usually in a solvent. The proportions of compounds (2) and (3) are not specifically limited, but usually about 0.9 to about 1.1 moles of compound (2) is used per mole of compound (3). Known amines are widely usable, for example, piperidine, morpholine, triethylamine, pyridine, lutidine, 1,4-diazabicyclo[2.2.2]octane, 1,5-diazabicyclo[4,3,0]nonene-5,1,8-diazabicyclo[5,4,0]-undecene-7 and the like. The amount of the amine can be suitably selected from a wide range, and usually about 1 to about 10 moles per mole of compound (2). The solvent is not limited specifically insofar as it can dissolve compounds (2) and (3). Examples are methanol, acetone, methyl ethyl ketone, ethyl acetate, butyl acetate, dichloromethane, dimethylformamide and the like. The condensation reaction is carried out at room temperature to the boiling point of the solvent used and is completed usually in about 1 to about 24 hours. The spiropyran compound thus obtained can be readily isolated and purified from the reaction mixture by conventional isolation and purification methods.

Among the spiropyran compounds represented by formula (1), following compounds are especially preferable.

3,5-Dimethyl-6'-nitrospiro[benzoselenazoline-2,2'(2'H)-1'-benzopyran]

8'-Methacryloxymethyl-3-methyl-6'-nitrospiro [benzoselenazoline-2,2'(2'H)-1'-benzopyran]

8'-Methacryloxymethyl-3,5-dimethyl-6'-nitrospiro [benzoselenazoline-2,2'(2'H)-1'-benzopyran]

8'-Methacryloxymethyl-5-methoxy-3-methyl-6'-nitrospiro[benzoselenazoline-2,2'(2'H)-1'-benzopyran]

8'-Methacryloxymethyl-6'-nitro-3-octadecylspiro-[benzoselenazoline-2,2'(2'H)-1'-benzopyran]

6-Amino-3,5-dimethyl-6'-nitrospiro[benzoselenazoline-2,2'(2',H)-1'-benzopyran]

6-Methylamino-3,5-dimethyl-6'-nitrospiro [benzoselenazoline-2,2'(2'H)-1'-benzopyran]

6-Dimethylamino-3,5-dimethyl-6'-nitrospiro [benzoselenazoline-2,2'(2'H)-1'-benzopyran]

6-Dimethylamino-3-octadecyl-6'-nitrospiro [benzoselenazoline-2,2'(2'H)-1'-benzopyran]

6-Dimethylamino-3-isopropyl-6'-nitrospiro [benzoselenazoline-2,2'(2',H)-1'-benzopyran]

8'-Methacryloxymethyl-6-dimethylamino-3,5-dimethyl-6'-nitrospiro[benzoselenazoline-2,2'(2'H)-1'-benzopyran]

8'-Vinyl-6-dimethylamino-3,5-dimethyl-6'-nitrospiro-[benzoselenazoline-2,2'(2'H)-1'-benzopyran]

8'-Hydroxymethyl-6-dimethylamino-3,5-dimethyl-6'-nitrospiro[benzoselenazoline-2,2'(2'H)-1'-benzopyran]

4,6-Di(dimethylamino)-3,5-dimethyl-6'-nitrospiro-[benzoselenazoline-2,2'(2'H)-1'-benzopyran]

6-Dimethylamino-3-hydroxyethyl-6'-nitrospiro [benzoselenazoline-2,2'(2'H)-1'-benzopyran]

6-Dimethylamino-3-methacryloxyethyl-6'-nitrospiro [benzoselenazoline-2,2'(2'H)-1'-benzopyran]

3-Methacryloxyethyl-5-methoxy-6-dimethylamino-6'-nitrospiro[benzoselenazoline-2,2'(2'H)-1'-benzopyran]

8'-Methacryloxymethyl-6-dimethylamino-5-methyl-6'-nitro-3-octadecylspiro[benzoselenazoline-2,2'(2'H)-1'-benzopyran]

8'-Vinyl-6-dimethylamino-5-methyl-6'-nitro-3-octadecylspiro[benzoselenazoline-2,2'(2'H)-1'-benzopyran]

6-Dimethylamino-3,5-dimethyl-6'-nitrospiro [benzoselenazoline-2,2'(2'H)-1'-benzothiopyran]

8'-Methacryloxymethyl-6-dimethylamino-3,5-dimethyl-6'-nitro-3-octadecylspiro[benzoselenazoline-2,2'(2'H)-1'-benzothiopyran]

Compound (2) for use as a starting material for spiropyran compound (1) is a known compound which can be readily prepared, for example, by reacting a corresponding 2-methylbenzoselenazole derivative with at least 1 mole, preferably 1.05 to 1.5 moles of the compound of the formula $R^1Y$ (wherein $R^1$ and Y are as defined above) per mole of said derivative in a solvent such as chloroform and the like in a sealed tube at about 50° to about 150° C. for 10 to 48 hours. The 2-methylbenzoselenazole derivative is a known compound disclosed, for example, in Ber., 46, 94 (1913), J. Amer. Chem. Soc., 68, 1536 (1946), the specification of the G. B. Patent No. 1411957 and the like, or a compound easily prepared by the methods described in said literature.

As will be more specifically illustrated in the following reference examples 1 to 5, a commercially available or synthesized benzoselenazole derivative can be used as such, or desired substituents can be introduced on the aromatic ring of the commercially available or synthesized benzoselenazole derivative. The substituents can be introduced, for example, by a suitable combination of known methods such as (a) nitration by the reaction with concentrated nitric acid, sodium nitrate and the like, (b) amination, (c) alkylation, (d) in particular, alkylation by the reaction with an alkylating agent such as alkyl iodide, toluenesulfonic acid ester and the like.

Compound (3) for use as the other starting material is a known compound which is easily synthesized or available. The following reaction schema-2 shows one of the methods for synthesizing compound (3).

Reaction Schema-2

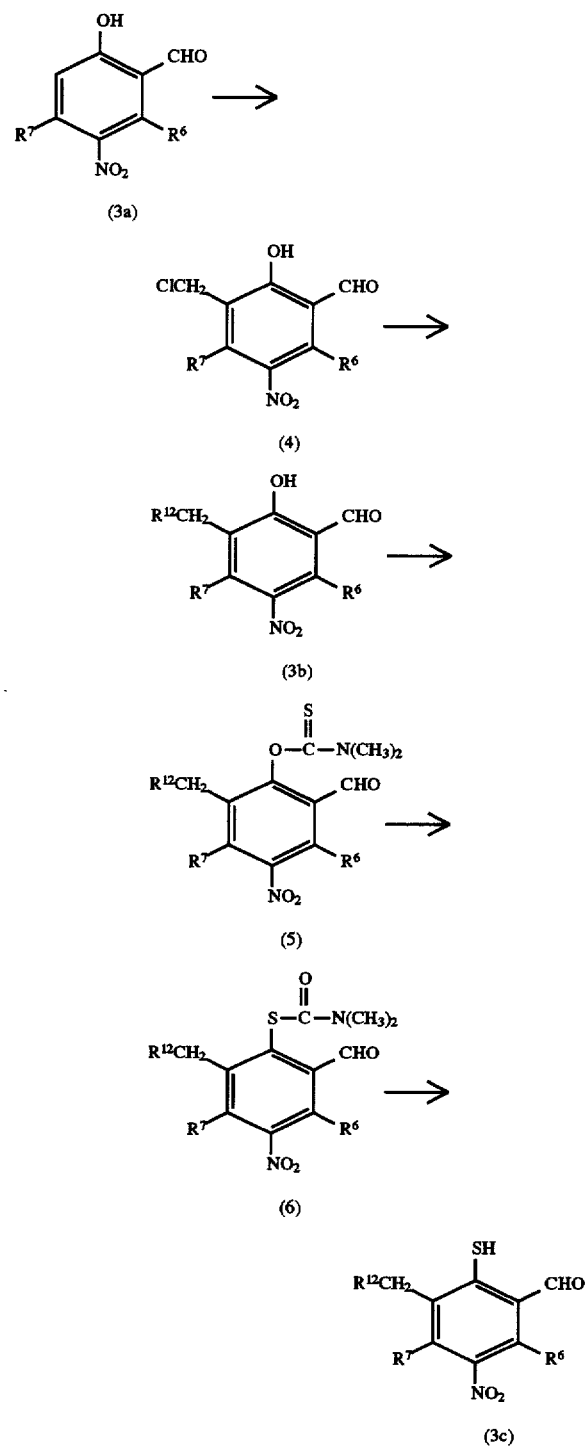

wherein $R^6$, $R^7$ and $R^8$ are as defined above and $R^{12}$ means a group —$OR^9$ or a group —$OCOC(R^{10})=CH_2$ (wherein $R^9$ and $R^{10}$ are as defined above).

Thus, a salicylaldehyde derivative (3a) is reacted with chloromethyl methyl ether to give a 3-chloromethyl-5-nitrosalicylaldehyde derivative (4), which is then reacted with a compound represented by the formula $R^{12}M$ (wherein $R^{12}$ is as defined above, and M is a metallic atom or a hydrogen atom), giving a 5-nitrosalicylaldehyde derivative (3b) wherein X is an oxygen atom. In the above formula, the metallic atom represented by M is, for example, an alkali metal, an alkali earth metal, silver and the like. Specific examples of the compound represented by $R^{12}M$ include silver acrylate, silver methacrylate, sodium acrylate, sodium methacrylate, sodium methylate, sodium ethylate, sodium n-propylate, sodium iso-propylate, sodium n-butylate, sodium iso-butylate, sodium tert-butylate, acrylic acid, methacrylic acid, methanol, ethanol, n-propanol, iso-propanol, n-butanol, iso-butanol, tert-butanol and the like.

Compound (3c) wherein X is a sulfur atom can be prepared by a method disclosed, for example, in Japanese Unexamined Patent Publication No. 54388/1985. Thus, a 5-nitrosalicylaldehyde derivative (3b) is reacted with N,N-dimethylthiocarbamoyl halide to obtain a 2-O-(N,N-dimethylthiocarbamoyl)benzaldehyde derivative (5). The obtained derivative is heated for isomerization, giving a 2-S-(N,N-dimethylthiocarbamoyl)benzaldehyde derivative (6), which is subsequently subjected to alkali hydrolysis to obtain compound (3c).

Compound (3) wherein $R^8$ is a nitro group can be easily prepared by a method disclosed, for example, in Japanese Unexamined Patent Publication No. 76490/1986, Published Searched Application No. 813072/1991 and the like. Thus, compound (3) can be easily prepared by reacting 3-chloromethyl-5-nitrosalicylaldehyde derivative (4) obtained according to reaction schema-2 with triphenylphosphine to give a triphenylphosphonium chloride derivative, which is subsequently reacted with paraformaldehyde in the presence of a base such as an alkali metal hydroxide and the like.

Compound (3) wherein $R^8$ is a hydroxymethyl group can be prepared by hydrolyzing 3-chloromethyl-5-nitrosalicylaldehyde derivative (4) in the presence of silver nitrate, sodium hydrogencarbonate or the like in a conventional manner.

The spiropyran compound salt of the present invention can be made into an optical material by mixing one or more species of the spiropyran compound salt of the invention with a suitable matrix material such as a resin, an organic solvent and the like. Usable matrix resins are not limited specifically insofar as the salt of the invention can be uniformly dispersed therein. Specific examples of the matrix resins include polymethacrylic acid, polyacrylic acid, a $C_1$ to $C_8$ alkyl ester of polymethacrylic acid or polyacrylic acid, polyacrylonitrile, polyacrylic acid amide, poly N,N-dimethylacrylamide, polyvinyl acetate, polystyrene, poly α-methylstyrene, polyvinyltoluene, polyvinyl alcohol, polyvinyl butyral, polyvinyl pyrrolidone, polyvinyl chloride, polyvinilidene chloride, polycarbonate, polyethylene oxide, nylon, polyurethane, various polyolefins, ethyl cellulose and the like. Two or more of these resins can be used in mixture. The amount of the spiropyran compound salt of the invention to be mixed with the resin is not limited specifically and can be suitably selected from a wide range, but is usually about 0.01 to about 30% by weight, preferably about 0.1 to about 15% by weight, based on the total amount of the salt and the resin. When the spiropyran compound salt of the present invention is mixed with a resin or an organic solvent, various additives can be added which are conventionally used in compositions for optical materials within the range which does not adversely affect the properties of the salt of the invention.

The resin composition containing the spiropyran compound salt of the invention can be formed into a desired shape as such, or can be applied by coating to a suitable substrate such as a metal, a ceramic, a plastic, paper and the like. The coating can be carried out by various methods such as spin coating, spray coating, dip coating, flow coating, bar coating and the like. A clear protective coating film may be provided on the coating film of the resin composition containing the spiropyran compound salt of the invention.

The optical material containing the spiropyran compound salt of the invention can be used as encapsulated or sealed in a suitable container by a known method. The obtained capsules can be used as mixed with resins or other matrix materials.

Among the spiropyran compound salts of the present invention, the species substituted by a polymerizable group can be homopolymerized or copolymerized with a comonomer copolymerizable with said spiropyran compound salt. Preferred copolymerizable monomers include, for example, methacrylic acid, acrylic acid, a $C_1$ to $C_8$ alkylester of methacrylic acid or acrylic acid, acrylonitrile, acrylic acid amide, N,N-dimethylacrylamide, vinyl acetate, styrene, α-methylstyrene, vinyltoluene and the like. The obtained polymer can be used as optical and mechanical elements.

According to the present invention, there is provided a compound which is very useful as an optical material, the compound having the maximum absorption wavelength at 400 to 500 nm and showing high sensitivity to light in this wavelength region.

BEST MODE FOR CARRYING OUT THE INVENTION

Figure 1:
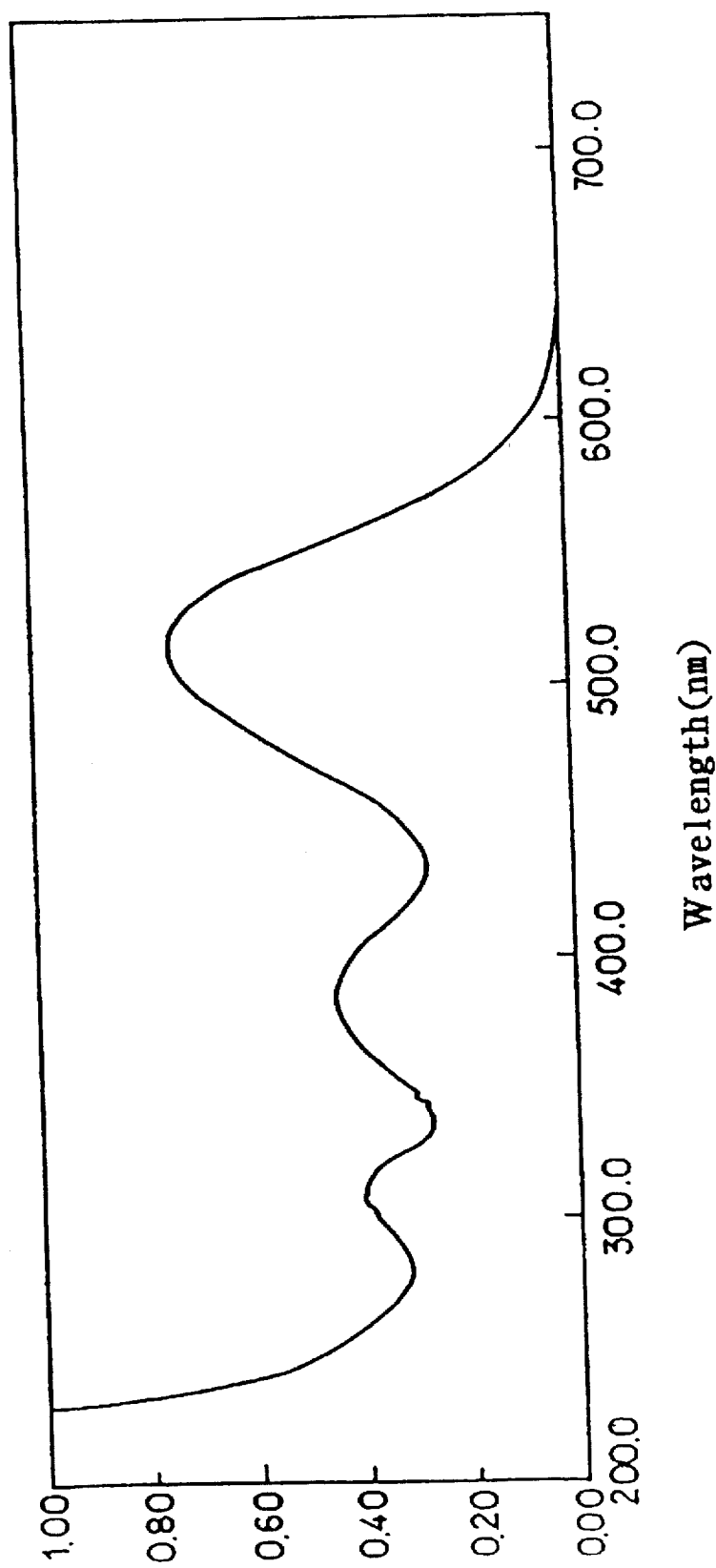
FIG. 1 is the ultraviolet visible absorption spectrum of the compound of Example 1 as dissolved in methanol.

The following reference examples and examples illustrate the present invention in further detail.

REFERENCE EXAMPLE 1

Synthesis of 2,5-dimethyl-6-nitrobenzoselenazole

A 4.94 g quantity of 2,5-dimethylbenzoselenazole was added to 25 ml of ice-cooled sulfuric acid, and the mixture was stirred to obtain a solution. To the solution was added dropwise a cooled solution of 2.27 g of sodium nitrate in 20 ml of sulfuric acid, followed by stirring for 2 hours with ice-cooling. The reaction mixture was added dropwise to 650 ml of an ice-cooled aqueous solution of 3N sodium hydroxide to adjust the reaction mixture to pH 11 or more. The reaction mixture was subjected to extraction with benzene, and the extract was washed with saturated saline solution and dried over anhydrous sodium sulfate. Then, the solvent was distilled off, giving 5.88 g of a mixture of 2,5-dimethyl-6-nitrobenzoselenazole and 2,5-dimethyl-4-nitrobenzoselenazole as pale yellow solids (yield 100%), however, $^1$H-NMR spectrum revealed that 2,5-dimethyl-6-nitrobenzoselenazole:2,5-dimethyl-4-nitrobenzoselenazole ratio was 58:42).

$^1$H-NMR (400 MHz, CDCl$_3$): δ ppm;

2,5-dimethyl-6-nitrobenzoselenazole; 2.70 (s, 5-CH$_3$, 3H), 2.89 (s, 2-CH$_3$, 3H), 7.88 (s, phenyl, 1H), 8.52 (s, phenyl, 1H)

2,5-dimethyl-4-nitrobenzoselenazole; 2.45 (s, 5-CH$_3$, 3H), 2.87 (s, 2-CH$_3$, 3H), 7.20 (d, phenyl, 1H), 7.83 (d, phenyl, 1H)

REFERENCE EXAMPLE 2

Synthesis of 6-amino-2,5-dimethylbenzoselenazole

A 5.88 g quantity of the 2,5-dimethylnitrobenzoselenazole mixture obtained in reference example 1 was added to 143 ml of ice-cooled hydrochloric acid, followed by stirring. To the obtained solution was gradually added 5.47 g of tin powder, and the mixture was further stirred for 2.5 hours with ice-cooling. The reaction mixture was added dropwise to 650 ml of an ice-cooled aqueous solution of 3N sodium hydroxide to adjust the reaction mixture to pH 11 or more. The obtained mixture was subjected to extraction with benzene, and the extract was washed with saturated saline solution and dried over sodium carbonate. Then, the solvent was distilled off, giving 5.18 g of pale yellow-white solids (crude yield 100%). The solids were then isolated and purified by silica gel column chromatography to obtain 2.59 g of 6-amino-2,5-dimethylbenzoselenazole as pale yellow-white solids (yield 50%).

$^1$H-NMR (400 MHz, CDCl$_3$): δ ppm;

2.26 (s, 5-CH$_3$, 3H), 2.77 (s, 2-CH$_3$, 3H), 3.70 (s, amino, 2H), 7.09 (s, phenyl, 1H), 7.64 (s, phenyl, 1H)

REFERENCE EXAMPLE 3

Synthesis of 6-dimethylamino-2,5-dimethylbenzoselenazole

A 2.24 quantity of 6-amino-2,5-dimethylbenzoselenazole was dissolved in a mixture of 114 ml of acetonitrile and 14.3 ml of 37% formalin by stirring. To the solution was added 2.64 g of sodium cyanoborohydride and 1.14 ml of acetic acid, and the mixture was stirred at room temperature for 2.5 hours. Then, 1.14 ml of acetic acid was further added, followed by further stirring at room temperature for 1 hour. After distilling off the solvent and the like, 300 ml of diethyl ether was added, and the mixture was washed successively with 1N sodium hydroxide and saturated saline solution and dried over potassium carbonate. Then, the solvent was distilled off, giving 2.69 g of a yellow viscous product. The product was isolated and purified by silica gel column chromatography, giving 2.16 g of 6-dimethylamino-2,5-dimethylbenzoselenazole as a pale yellow oil (yield 86%).

$^1$H-NMR (400 MHz, CDCl$_3$): δ ppm;

2.42 (s, 5-CH$_3$, 3H), 2.73 (s, dimethylamino, 6H), 2.81 (s, 2-CH$_3$, 3H), 7.46 (s, phenyl, 1H), 7.74 (s, phenyl, 1H)

REFERENCE EXAMPLE 4

Synthesis of 6-dimethylamino-2,3,5-trimethylbenzoselenazolenium iodide

An autoclave was charged with 1.06 g of 6-dimethylamino-2,5-dimethylbenzoselenazole, 2.42 g of methyl iodide and 45 ml of chloroform. Then, the air in the autoclave was displaced by argon gas and the tube was sealed. After carrying out the reaction at 80° C. for 8 days, the solvent was distilled off and the residue was washed with diethyl ether, giving 1.55 g of 6-dimethylamino-2,3,5-trimethylbenzoselenazolenium iodide as pale yellow solids (yield 94%).

$^1$H-NMR (400 MHz, DMSO-d$_6$): δ ppm;

2.46 (s, 5-CH$_3$, 3H), 2.73 (s, dimethylamino, 6H), 3.08 (s, 2-CH$_3$, 3H), 4.07 (s, 3-CH$_3$, 3H), 8.00 (s, phenyl, 1H), 8.04 (s, phenyl, 1H)

EXAMPLE 1

Synthesis of 6-dimethylamino-3,5-dimethyl-6'-nitrospiro [benzoselenazoline-2,2'(2'H)-1'-benzopyran)

In a dark place and in a nitrogen gas stream, 2.95 g of 6-dimethylamino-2,3,5-trimethylbenzoselenazolenium iodide and 1.27 g of 5-nitrosalicylaldehyde were suspended in 900 ml of dry methanol. After dropwise addition of 1.01 g of piperidine, the mixture was reacted at 80° C. for 23 hours. After distilling off the solvent, the residue was washed with water and dried, giving 2.76 g of 6-dimethylamino-3, 5-dimethyl-6'-nitrospiro[benzoselenazoline-2,2'(2'H)-1'-benzopyran] as dark purple solids (yield 89%).

$^1$H-NMR(400 MHz, DMSO-$d_6$): δ ppm;

2.41 (s, 5-$CH_3$, 3H), 2.72 (s, dimethylamino, 6H), 4.02 (s, 3-$CH_3$, 3H), 6.18 (d, phenyl, 1H), 7.76 (dd, phenyl, 1H), 7.83 (s, phenyl, 1H), 7.90 (s, phenyl, 1H), 7.98 (d, olefin, 1H), 8.42 (d, phenyl, 1H), 8.60 (d, olefin, 1H)

The ultraviolet visible absorption spectrum of the obtained compound as dissolved in methanol is shown in FIG. 1.

UV ($CH_3OH$): λmax=512 nm, ε=29500$M^{-1}cm^{-1}$

EXAMPLE 2

Synthesis of 6-dimethylamino-3,5-dimethyl-6'-nitrospiro-[benzoselenazoline-2,2'(2'H)-1'-benzopyran] .dihydrochloride In a dark place, 2.71 g of 6-dimethylamino-3,5-dimethyl-6'-nitrospiro[benzoselenazoline-2,2'(2'H)-1'-benzopyran] was suspended in a mixed solvent of 300 ml of chloroform and 180 ml of methanol. To the suspension was added dropwise 170 ml of a 2% hydrochloric acid solution in methanol, giving a red solution. The solvent and excess hydrochloric acid were distilled off under reduced pressure, and the residue was fully washed with diethyl ether and dried, giving 3.18 g of 6-dimethylamino-3,5-dimethyl-6'-nitrospiro[benzoselenazoline-2,2'(2'H)-1'-benzopyran] .dihydrochloride as brown solids (yield 100%).

$^1$H-NMR (400 MHz, DMSO-$d_6$): δ ppm;

2.48 (s, 5-$CH_3$, 3H), 2.81 (s, dimethylamino, 6H), 4.25 (s, 3-$CH_3$, 3H), 7.32 (d, phenyl, 1H), 8.07 (s, phenyl, 1H), 8.14–8.16 (olefin+phenyl, 3H), 8.23 (dd, phenyl, 1H), 8.89 (d, phenyl, 1H)

$^1$H-NMR(400 MHz, $CD_3OD$): δ ppm;

2.78 (s, 5-$CH_3$, 3H), 3.36 (s, dimethylamino, 6H), 4.36 (s, 3-$CH_3$, 3H), 7.13 (d, phenyl, 1H), 8.21 (s, olefin, 1H), 8.26 (s, phenyl, 1H), 8.29 (dd, phenyl, 1H), 8.37 (d, olefin, 1H), 8.68 (s, phenyl, 1H), 8.83 (d, phenyl, 1H)

Figure 2:
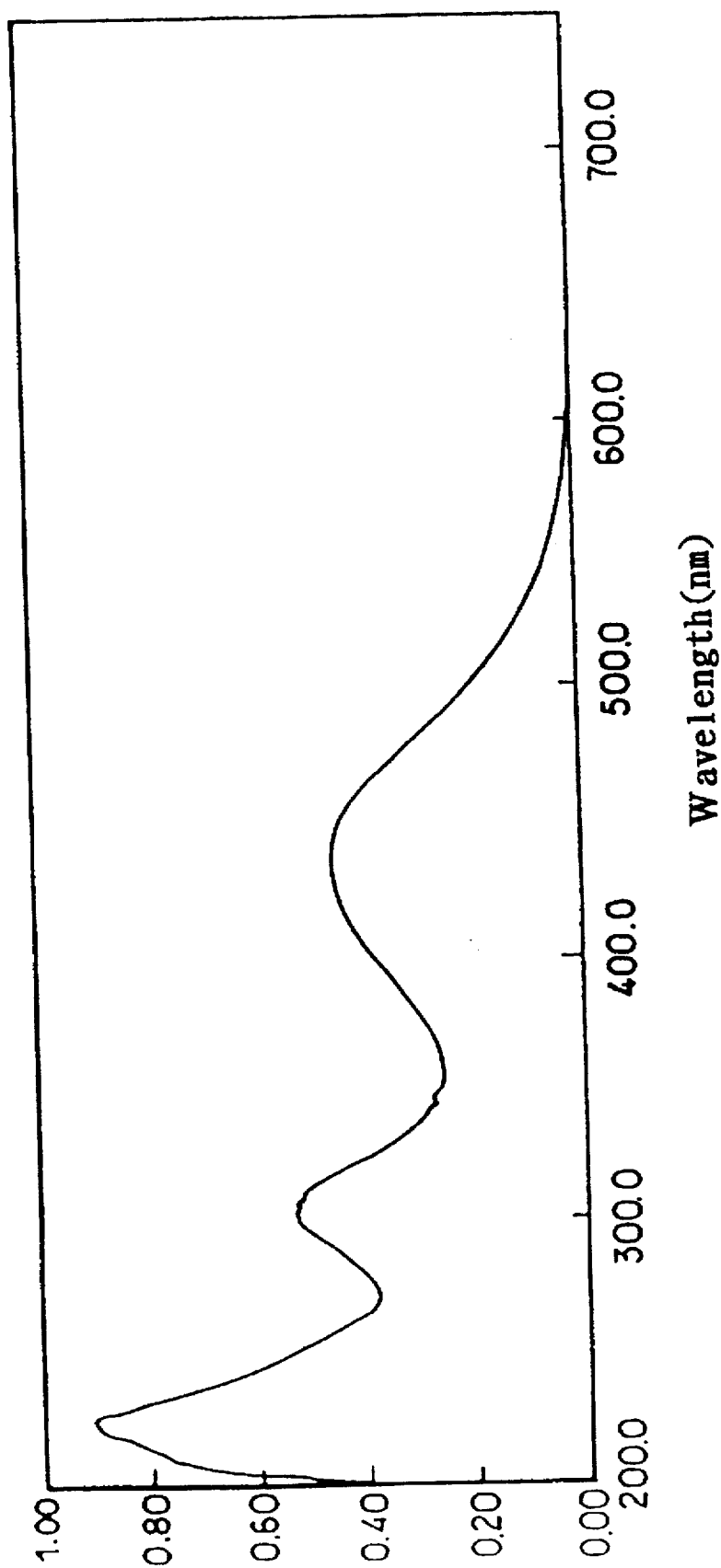
FIG. 2 is the ultraviolet visible absorption spectrum of the compound of Example 2 as dissolved in methanol.

The ultraviolet visible absorption spectrum of the obtained compound as dissolved in methanol is shown in FIG. 2.

UV ($CH_3OH$): λmax=420 nm, ε=17100$M^{-1}cm^{-1}$

REFERENCE EXAMPLE 5

Synthesis of 3-hydroxymethyl-5-nitrosalicylaldehyde

In a dark place, 0.5 g of 3-chloromethyl-5-nitrosalicylaldehyde was dissolved in a mixture of 4 ml of acetone and 1 ml of distilled water at room temperature, followed by dropwise addition of a solution of 0.40 g of silver nitrate in 2 ml of distilled water. After stirring at room temperature for 1.5 hours, the precipitated white solids were collected by filtration and fully washed with acetone. Acetone was distilled off from the obtained acetone solution under reduced pressure and the residue was dried, giving 0.37 g of 3-hydroxymethyl-5-nitrosalicylaldehyde as pale ocher solids (yield 87%).

$^1$H-NMR (400 MHz, DMSO-$d_6$): δ ppm;

4.64 (s, $CH_2$, 2H), 8.50 (phenyl, 2H), 10.04 (s, aldehyde, 3H), 11.70 (br, phenolic OH, 1H)

EXAMPLE 3

Synthesis of 8'-hydroxymethyl-6-dimethylamino-3,5-dimethyl-6'-nitrospiro[benzoselenazoline-2,2'-(2'H)-1'-benzopyran]

In a dark place and in a nitrogen stream, 0.30 g of 6-dimethylamino-2,3,5-trimethylbenzoselenazolenium iodide and 0.16 g of 3-hydroxymethyl-5-nitrosalicylaldehyde were suspended in 30 ml of dry methanol. After dropwise addition of 0.022 g of piperidine, the mixture was reacted at room temperature for an hour, and then at 70° C. for 11 hours. The reaction mixture was allowed to cool, and the precipitated solids were collected by filtration, washed with cold methanol and dried, giving 0.27 g of 8'-hydroxymethyl-6-dimethylamino-3,5-dimethyl-6'-nitrospiro[benzoselenazoline-2,2'(2'H)-1'-benzopyran] as dark red-brown solids (yield 80%).

$^1$H-NMR(400 MHz, DMSO-$d_6$): δ ppm;

2.43 (s, 5-$CH_3$, 3H), 2.73 (s, dimethylamino, 6H), 4.04 (s, 3-$CH_3$, 3H), 4.37 (s, $CH_2$, 2H), 7.84 (s, phenyl, 1H), 7.88 (d, phenyl, 1H), 7.92 (s, phenyl, 1H), 8.03 (d, olefin, 1H), 8.42, (d, phenyl, 1H), 8.61 (d, olefin, 1H)

UV ($CH_3OH$): λmax=521 nm, ε=29400$M^{-1}cm^{-1}$

EXAMPLE 4

Synthesis of 8'-hydroxymethyl-6-dimethylamino-3,5-dimethyl-6'-nitrospiro[benzoselenazoline-2,2'(2'H)-1'-benzopyran].monohydrochloride In a dark place, 0.059 g of 8'-hydroxymethyl-6-dimethylamino-3,5-dimethyl-6'-nitrospiro [benzoselenazoline-2,2'(2'H)-1'-benzopyran] was suspended in 4.0 ml of tetrahydrofuran. To the suspension was added dropwise 1.0 ml of 0.112N hydrochloric acid, and the mixture was stirred at room temperature for 8 hours. The precipitated suspended solids were collected by filtration, fully washed with diethyl ether and dried. The obtained solids were dissolved in 1.0 ml of methanol and the solution was added dropwise to 20 ml of diethyl ether. The precipitated solids were collected by filtration and dried, giving 0.041 g of 8'-hydroxymethyl-6-dimethylamino-3,5-dimethyl-6'-nitrospiro[benzoselenazoline-2,2'-(2'H)-1'-benzopyran].monohydrochloride as red-brown solids (yield 76%).

$^1$H-NMR (400 MHz, DMSO-$d_6$): δ ppm;

2.49 (s, 5-$CH_3$, 3H+DMSO), 2.78 (s, dimethylamino, 6H), 4.29 (s, 3-$CH_3$, 3H), 4.63 (s, $CH_2$, 2H), 8.04–8.06 (s+d, phenyl, 2H), 8.12 (d, olefin, 1H), 8.30–8.34 (s+d, phenyl+ olefin, 2H), 8.85 (d, phenyl, 1H)

UV ($CH_3OH$): λmax=456 nm, ε=18700$M^{-1}cm^{-1}$

Figure 3:
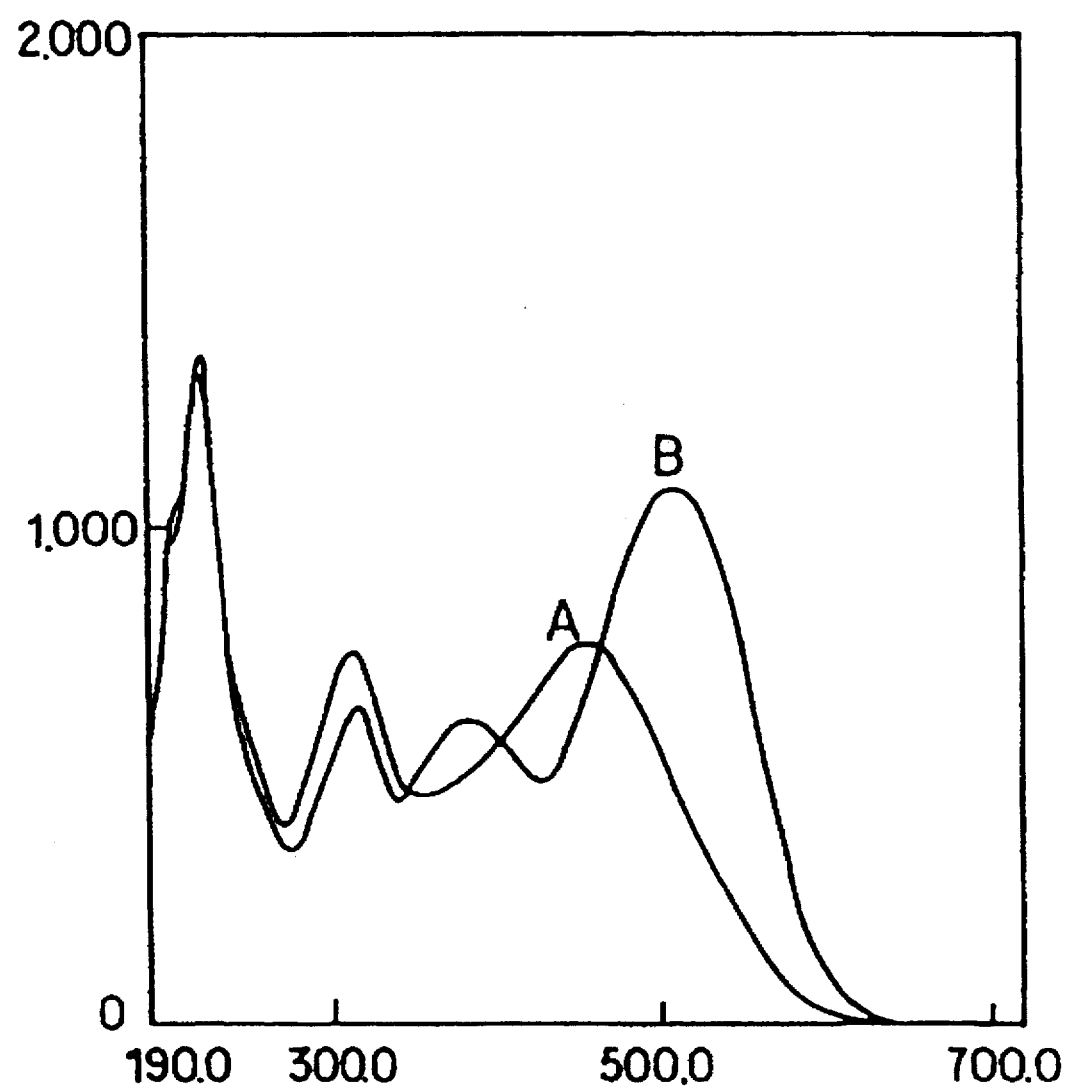
FIG. 3 is the ultraviolet visible absorption spectrum of the compound of Example 4.

When 2.14 mg of 8'-hydroxymethyl-6-dimethylamino-3, 5-dimethyl-6'-nitrospiro[benzoselenazoline-2,2'(2'H)-1'-benzopyran].monohydrochloride was dissolved in 100 ml of methanol, a spectrum was obtained which had the maximum absorption wavelength at 456 nm (FIG. 3-A).

When one equivalent of a triethylamine solution in methanol was added, the maximum absorption wavelength was shifted to a longer wavelength of 521 nm (FIG. 3-B). When one equivalent of a hydrochloric acid solution in methanol was further added, the maximum absorption wavelength was returned to 456 nm.

EXAMPLE 5

Synthesis of 8'-hydroxymethyl-6-dimethylamino-3,5-dimethyl-6'-nitrospiro[benzoselenazoline-2,2'(2'H)-1'-benzopyran].dihydrochloride In a dark place, 0.050 g of 8'-hydroxymethyl-6-dimethylamino-3,5-dimethyl-6'-nitrospiro[benzoselenazoline-2,2'(2'H)-1'-benzopyran] was suspended in 4.0 ml of tetrahydrofuran. To the suspension was added dropwise 1.0 ml of 3N hydrochloric acid, and the mixture was stirred at room temperature for 8 hours. The precipitated suspended solids were collected by filtration, fully washed with diethyl ether and dried. The solids were dissolved in 1.0 ml of methanol, and the solution was added dropwise to 20 ml of diethyl ether. The precipitated solids were then collected by filtration and dried, giving 0.041 g of 8'-hydroxymethyl-6-dimethylamino-3,5-dimethyl-6'-nitrospiro[benzoselenazoline-2,2'(2'H)-1'-benzopyran].dihydrochloride as yellow solids (yield 70%).

$^1$H-NMR(400 MHz, DMSO-$d_6$): δ ppm;

2.49 (s, 5-CH$_3$, 3H+DMSO), 2.79 (s, dimethylamino, 6H), 4.30 (s, 3-CH$_3$, 3H), 4.63 (s, CH$_2$, 2H), 8.05–8.07 (s+d, phenyl, 2H), 8.12 (d, olefin, 1H), 8.30 (s, phenyl, 1H), 8.36 (d, olefin, 1H), 8.86 (d, phenyl, 1H)

UV (CH$_3$OH): λmax=435 nm, ε=30200M$^{-1}$cm$^1$

EXAMPLE 6

Synthesis of 8'-methacryloxymethyl-6-dimethylamino-3,5-dimethyl-6'-nitrospiro[benzoselenazoline-2,2'(2'H)-1'-benzopyran]

In a dark place, 0.300 g of 6-dimethylamino-2,3,5-trimethylbenzoselenazolenium iodide and 0.204 g of 3-methacryloxymethyl-5-nitrosalicylaldehyde were suspended in 30 ml of dry methanol. To the suspension was added dropwise 0.063 g of piperidine, and the mixture was reacted at room temperature for 11 hours. The reaction mixture was allowed to cool, the precipitated solids were collected by filtration, washed with cold methanol and dried, giving 0.333 g of 8'-methacryloxymethyl-6-dimethylamino-3,5-dimethyl-6'-nitrospiro[benzoselenazoline-2,2'(2'H)-1'-benzopyran] as dark blue-purple solids (yield 82%).

$^1$H-NMR (400 MHz, DMSO-$d_6$): δ ppm;

1.91 (s, CH$_3$, 3H), 2.42 (s, 5-CH$_3$, 3H), 2.73 (s, dimethylamino, 6H), 4.05 (s, 3-CH$_3$, 3H), 5.03 (s, CH$_2$, 2H), 5.70 (s, vinyl, 1H), 6.06 (s, vinyl, 1H), 7.85 (s, phenyl, 1H), 7.86 (d, phenyl, 1H), 7.92 (s, phenyl, 1H), 8.03 (d, olefin, 1H), 8.46 (d, phenyl, 1H), 8.64 (d olefin, 1H)

UV (CH$_3$OH): λmax=519 nm, ε=28000M$^{-1}$cm$^{-1}$

Figure 4:
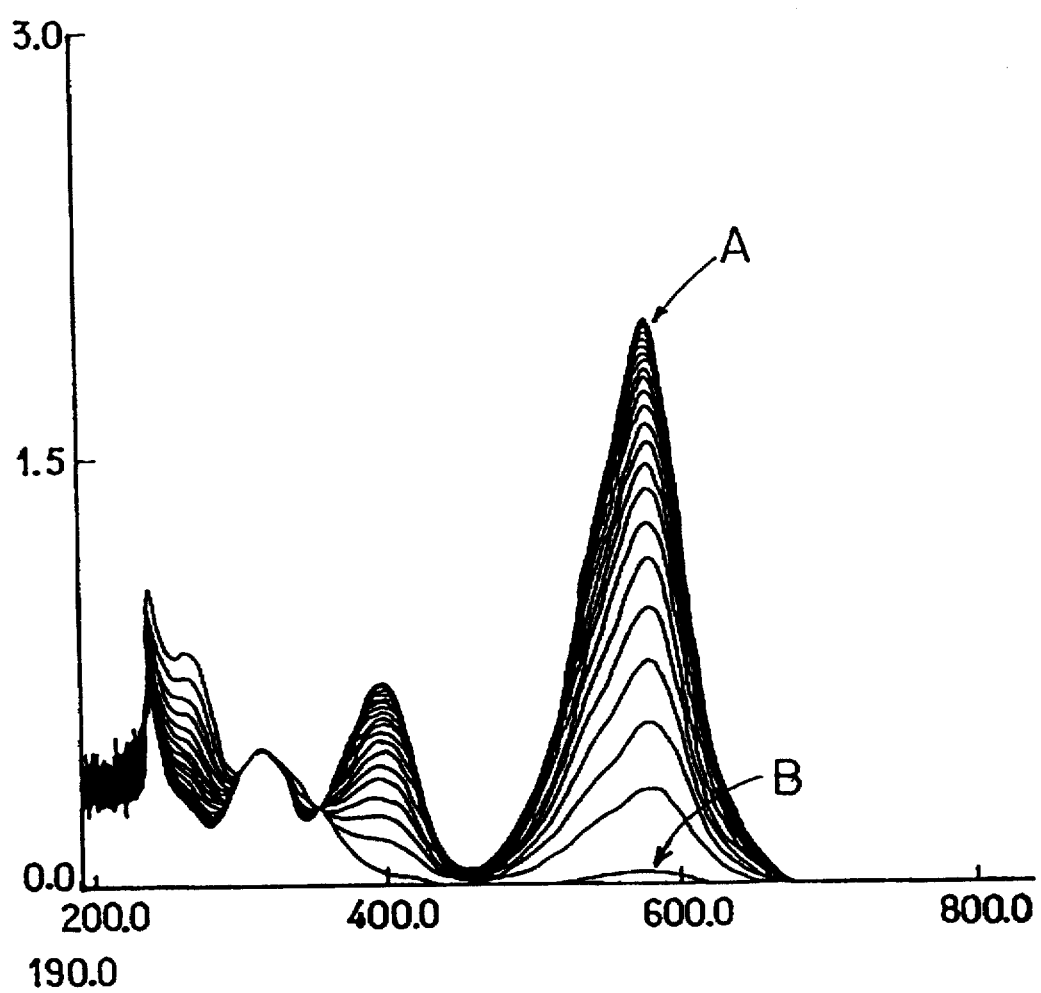
FIG. 4 is the ultraviolet visible absorption spectrum of the compound of Example 6.

When 1.95 mg of 8'-methacryloxymethyl-6-dimethylamino-3,5-dimethyl-6'-nitrospiro[benzoselenazoline-2,2'(2'H)-1'-benzopyran] was dissolved in 100 ml of chloroform, a spectrum was obtained which had the maximum absorption wavelength at 583 nm (FIG. 4-A). When this solution was irradiated with visible light for 10 seconds using a 500 W super-high-pressure mercury lamp fitted with a cutoff filter which transmits visible light of 400 nm or more, the maximum absorption wavelength disappeared and the solution became colorless and clear (FIG. 4-B). When maintaining at 25° C. for an hour, the solution returned to a blue-purple clear solution. The cycle consisting of the disappearance of color by irradiation with visible light and the color development at room temperature could be repeated with a good reproducibility.

EXAMPLE 7

Synthesis of 8'-methacryloxymethyl-6-dimethylamino-3,5-dimethyl-6'-nitrospiro[benzoselenazoline-2,2'(2'H)-1'-benzopyran].monohydrochloride In a dark place, 0.059 g of 8'-methacryloxymethyl-6-dimethylamino-3,5-dimethyl-6'-nitrospiro[benzoselenazoline-2,2'(2'H)-1'-benzopyran] was suspended in 4.0 ml of tetrahydrofuran. To the suspension was added dropwise 1.0 ml of 0.112N hydrochloric acid, and the mixture was stirred at room temperature for 7 hours. The precipitated suspended solids were collected by filtration, fully washed with diethyl ether and dried. The solids were dissolved in 1.0 ml of methanol, and the solution was added dropwise to 20 ml of diethyl ether. The precipitated solids were collected by filtration and dried, giving 0.044 g of 8'-methacryloxymethyl-6-dimethylamino-3,5-dimethyl-6'-nitrospiro[benzoselenazoline-2,2'(2'H)-1'-benzopyran].monohydrochloride as red-brown solids (yield 71%).

$^1$H-NMR(400 MHz, DMSO-$d_6$): δ ppm;

1.92 (s, CH$_3$, 3H), 2.46 (s, 5-CH$_3$, 3H), 2.77 (s, dimethylamino, 6H), 4.23 (s, 3-CH$_3$, 3H), 5.22 (s, CH$_2$, 2H), 5.74 (s, vinyl, 1H), 6.08 (s, vinyl, 1H), 7.99–8.00 (s+d, phenyl, 2H), 8.18–8.22 (s+d, phenyl+olefin, 2H), 8.31 (d, olefin, 1H), 8.81 (d, phenyl, 1H)

UV (CH$_3$OH): λmax=448 nm, ε=18700M$^{-1}$cm$^{-1}$

EXAMPLE 8

Synthesis of 8'-methacryloxymethyl-6-dimethylamino-3,5-dimethyl-6'-nitrospiro[benzoselenazoline-2,2'(2'H)-1'-benzopyran].dihydrochloride In a dark place, 0.059 g of 8'-methacryloxymethyl-6-dimethylamino-3,5-dimethyl-6'-nitrospiro[benzoselenazoline-2,2'(2'H)-1'-benzopyran] was suspended in 4.0 ml of tetrahydrofuran. To the suspension was added dropwise 1.0 ml of 3N hydrochloric acid, and the mixture was stirred at room temperature for 8 hours. The precipitated suspended solids were collected by filtration, fully washed with diethyl ether and dried. The solids were dissolved in 1.0 ml of methanol, and the solution was added dropwise to 20 ml of diethyl ether. The precipitated solids were collected by filtration and dried, giving 0.029 g of 8'-methacryloxymethyl-6-dimethylamino-3,5-dimethyl-6'-nitrospiro[benzoselenazoline-2,2'(2'H)-1'-benzopyran].dihydrochloride as red-brown solids (yield 43%).

$^1$H-NMR(400 MHz, DMSO-$d_6$): δ ppm;

1.92 (s, CH$_3$, 3H), 2.46 (s, 5-CH$_3$, 3H), 2.77 (s, dimethylamino, 6H), 4.24 (s, 3-CH$_3$, 3H), 5.22 (s, CH$_2$, 2H), 5.74 (s, vinyl, 1H), 6.08 (s, vinyl, 1H), 7.99–8.00 (s+d, phenyl, 2H), 8.18–8.22 (s+d, phenyl+olefin, 2H), 8.29 (d, olefin, 1H), 8.80 (d, phenyl, 1H)

UV (CH$_3$OH): λmax=443 nm, ε=17100M$^{-1}$cm$^{-1}$

EXAMPLE 9

Synthesis of 3,5-dimethyl-6'-nitrospiro[benzoselenazoline-2,2'(2'H)-1'-benzopyran]

In a dark place and in a nitrogen gas stream, 0.18 g of 2,3,5-trimethylbenzoselenazolenium iodide and 0.09 g of 5-nitrosalicylaldehyde were suspended in 30 ml of dry methanol. After dropwise addition of 0.05 g of piperidine, the mixture was reacted at 70° C. for 5 hours. After distilling off the solvent, the residue was washed with water and dried, giving 0.17 g of 3,5-dimethyl-6'-nitrospiro[benzoselenazoline-2,2'(2'H)-1'-benzopyran] as dark red-brown solids (yield 87%).

$^1$H-NMR(400 MHz, DMSO-$d_6$): δ ppm;

2.36 (s, 5-CH$_3$, 3H), 4.06 (s, 3-CH$_3$, 3H), 6.22 (d, phenyl, 1H), 7.41 (d, phenyl, 1H), 7.77 (dd, phenyl, 1H), 7.90 (s, phenyl, 1H), 8.09 (d, olefin, 1H), 8.16 (d, phenyl, 1H), 8.49 (d, phenyl, 1H), 8.66 (d, olefin, 1H)

UV (CH$_3$OH): λmax=513 nm

EXAMPLE 10

Synthesis of 3,5-dimethyl-6'-nitrospiro [benzoselenazoline-2,2'(2'H)-1'-benzopyran].hydrochloride A 0.05 g quantity of 3,5-dimethyl-6'-nitrospiro [benzoselenazoline-2,2'(2'H)-1'-benzopyran] was suspended in a mixed solvent of 5 ml of chloroform and 5 ml of tetrahydrofuran. To the suspension was added dropwise 1.0 ml of 6N hydrochloric acid, and the mixture was stirred at room temperature for 8 hours. The precipitated solids were collected by filtration, fully washed with diethyl ether and dried, giving 0.023 g of 2,5-dimethyl-6'-nitrospiro [benzoselenazoline-2,2'(2'H)-1'-benzopyran].hydrochloride as yellow solids (yield 44%).

$^1$H-NMR (200 MHz, DMSO-$d_6$): δ ppm;

1.72 (s, 5-CH$_3$, 3H), 3.46 (s, 3-CH$_3$, 3H), 6.43 (d, olefin, 1H), 6.73 (d, phenyl, 1H), 7.35 (d, phenyl, 1H), 7.35 (d, phenyl, 1H), 7.39 (s, phenyl, 1H), 7.42 (dd, phenyl, 1H), 7.50 (d, olefin, 1H), 8.09 (d, 1H, phenyl, 1H)

UV(CH$_3$OH): λmax=402 nm

Figure 5:
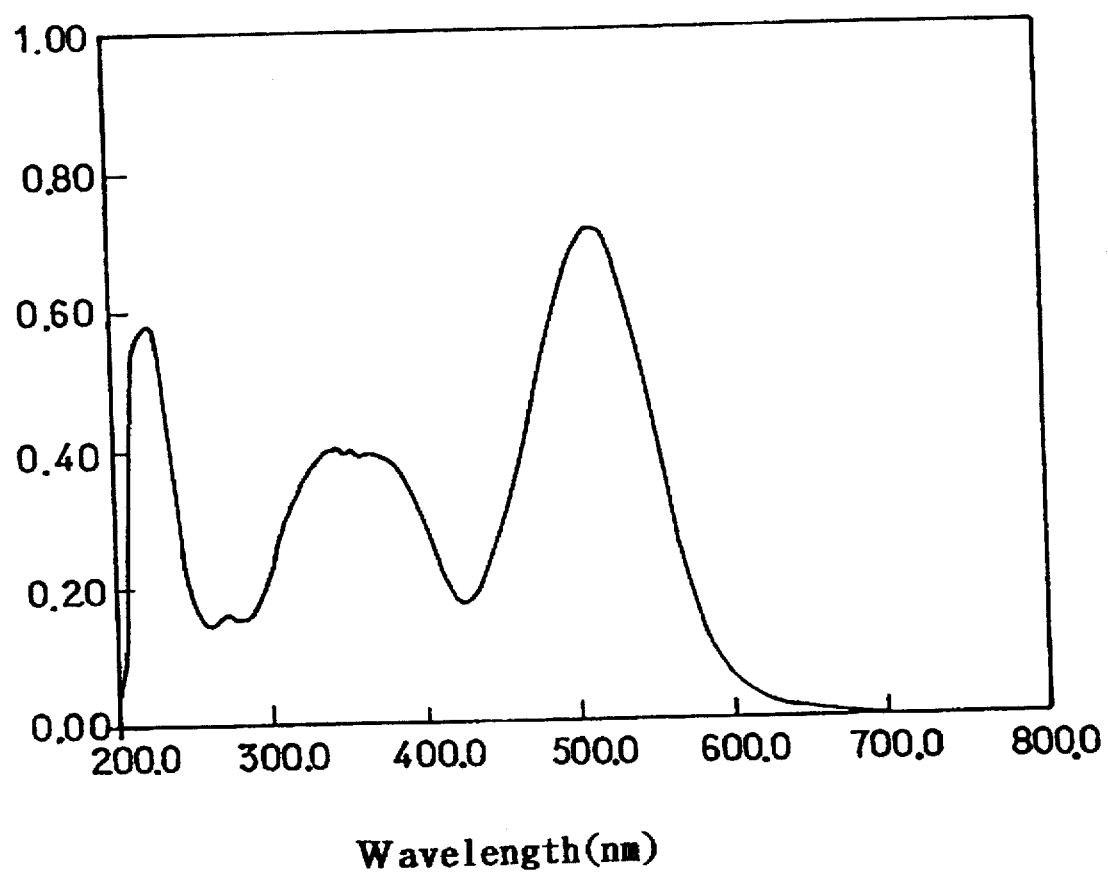
FIGS. 5 and 6 are the spectra of the compound obtained in Example 10.
Figure 6:
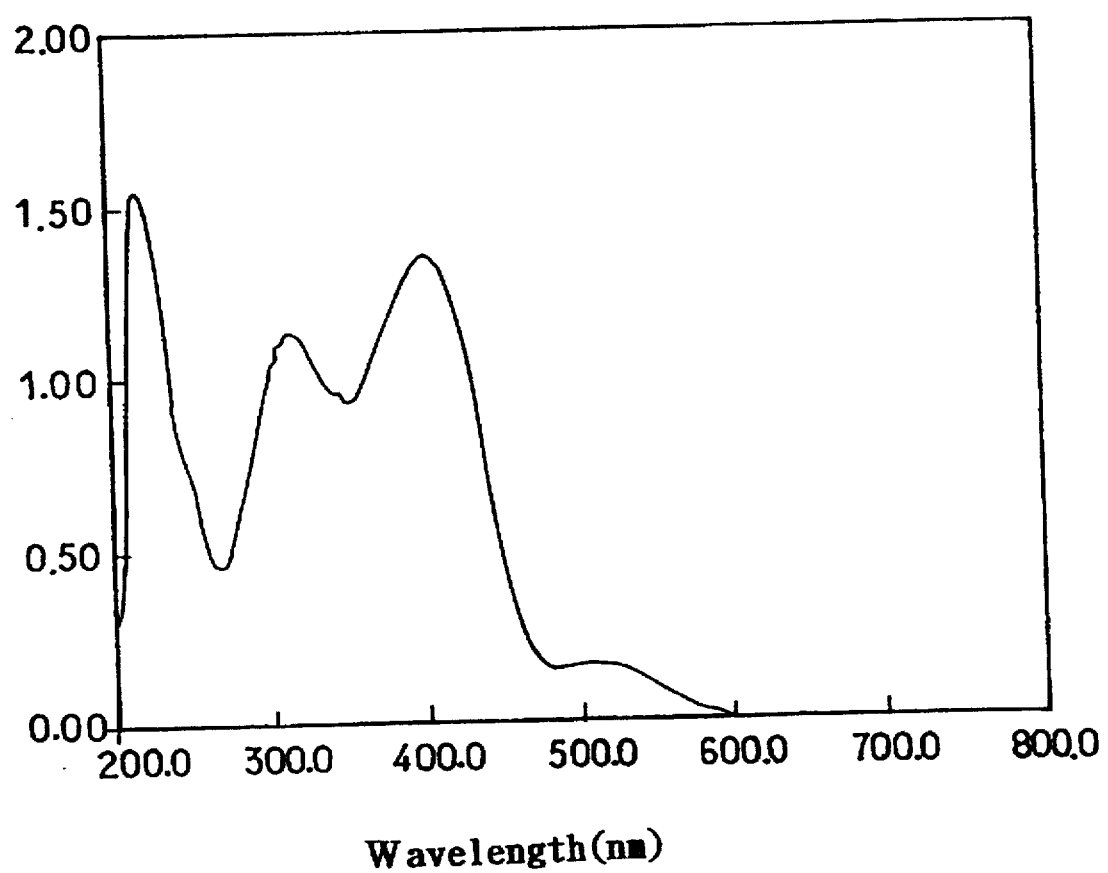

When one equivalent of a triethyl amine solution in methanol was added to a methanol solution of this compound, the maximum absorption wavelength was shifted to a longer wavelength of 513 nm (FIG. 5). When one equivalent of a hydrochloric acid solution in methanol was further added, the maximum absorption wavelength was returned to 402 nm (FIG. 6).

We claim:

1. A salt of a spiropyran compound and an acidic compound, the spiropyran compound being represented by the formula

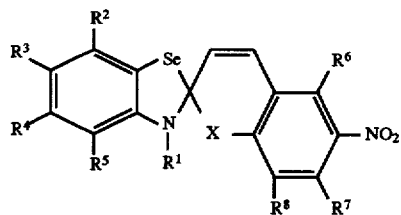

wherein R$^1$ means a C$_1$ to C$_{20}$ alkyl group, an aralkyl group, a hydroxyethyl group, an acryloxyethyl group or a methacryloxyethyl group, R$^2$ and R$^4$ are the same or different and each mean a hydrogen atom, a C$_1$ to C$_6$ alkyl group, an aryl group, an aralkyl group, a C$_1$ to C$_5$ alkoxy group, a halogen atom, a cyano group, a trichloromethyl group, a trifluoromethyl group or a nitro group, R$^3$ and R$^5$ are the same or different and each mean a hydrogen atom, a C$_1$ to C$_6$ alkyl group, an aryl group, an aralkyl group, a C$_1$ to C$_5$ alkoxy group, a halogen atom, a cyano group, a trichloromethyl group, a trifluoromethyl group, a nitro group, an amino group, a dimethylamino group or a diethyl amino group, R$^6$ and R$^7$ are the same or different and each mean a hydrogen atom, a C$_1$ to C$_6$ alkyl group, an aryl group, an aralkyl group, a halogen atom, a cyano group or a nitro group, R$^8$ means a hydrogen atom, a vinyl group, a group —CH$_2$OR$^9$ or a group —CH$_2$OCOC(R$^{10}$)=CH$_2$ (wherein R$^9$ means a hydrogen atom or a C$_1$ to C$_4$ alkyl group and R$^{10}$ means a hydrogen atom or a methyl group), and X means an oxygen atom or a sulfur atom.

2. The salt of a spiropyran compound and an acidic compound as defined in claim 1 wherein R$^1$ means a methyl group, an ethyl group, a n-propyl group, a n-octadecyl group, a hydroxyethyl group or a methacryloxyethyl group, R$^2$ means a hydrogen atom, R$^3$ means a hydrogen atom, a methyl group, a methoxy group, a nitro group, an amino group, a dimethylamino group or a diethylamino group, R$^4$ means a hydrogen atom, a methyl group or a methoxy group, R$^5$ means a hydrogen atom, a nitro group, an amino group, a dimethylamino group or a diethylamino group, R$^6$ and R$^7$ each mean a hydrogen atom, R$^8$ means a hydrogen atom, a vinyl group, a hydroxymethyl group or a methacryloxymethyl group, and X means an oxygen atom or a sulfur atom.

* * * * *